United States Patent
Du et al.

(10) Patent No.: US 12,193,380 B2
(45) Date of Patent: Jan. 14, 2025

(54) HORMONE-FREE CULTURE METHOD FOR CITRUS SHOOT TIP

(71) Applicant: Nanchong Academy of Agricultural Sciences, Nanchong (CN)

(72) Inventors: Xiaoqiu Du, Nanchong (CN); Ying He, Nanchong (CN); Defu Li, Nanchong (CN); Yue Liu, Nanchong (CN); Guichuan Yang, Nanchong (CN)

(73) Assignee: Nanchong Academy of Agricultural Sciences, Nanchong (CN)

( * ) Notice: Subject to any disclaimer, the term of this patent is extended or adjusted under 35 U.S.C. 154(b) by 140 days.

(21) Appl. No.: 18/131,391

(22) Filed: Apr. 6, 2023

(65) Prior Publication Data
US 2023/0397559 A1    Dec. 14, 2023

(51) Int. Cl.
*A01H 4/00* (2006.01)
*A01G 2/30* (2018.01)

(52) U.S. Cl.
CPC .............. *A01H 4/008* (2013.01); *A01G 2/30* (2018.02)

(58) Field of Classification Search
CPC .......... A01H 4/008; A01H 4/003; A01G 2/30; A01G 2/10; A01G 2/35
See application file for complete search history.

(56) References Cited

FOREIGN PATENT DOCUMENTS

| CN | 106973704 A | * | 7/2017 | ............... A01C 1/00 |
| CN | 112088671 A | * | 12/2020 | |
| CN | 117859649 A | * | 4/2024 | |

* cited by examiner

*Primary Examiner* — Trinh T Nguyen
(74) *Attorney, Agent, or Firm* — Bayramoglu Law Offices LLC

(57) ABSTRACT

A hormone-free culture method for a citrus shoot tip is provided according to the following steps: (1) selecting a citrus branch to make an explant; (2) washing with sterile water after disinfection; (3) inserting the explant into a Murashige and Skoog (MS) solid medium and culturing to produce a branch with new buds; (4) preparing a Murashge and Tucker (MT) liquid medium solution, where a mass concentration of sucrose is 7-8%; (5) removing an outer leave of the new bud, cutting and taking a shoot tip, and inoculating in a liquid medium for primary culture; (6) selecting a seed of a trifoliate orange or a citrange and peeling off a testa; washing with the sterile water after disinfection; (7) inoculating a resulting seed into a test tube containing the MS solid medium and culturing in dark to obtain an etiolated seedling; (8) cutting a T-shaped incision and placing the shoot tip in a middle of the T-shaped incision to obtain a grafted seedling; and (9) grafting culture, and then conducting a secondary grafting in a greenhouse when a scion bud grows to 0.5-1 cm. According to the present invention, regenerated seedlings are obtained without using hormones, and the efficiency of plant shoot tip culture is significantly improved, which makes the method of the present invention widely used in different citrus varieties.

8 Claims, 2 Drawing Sheets

HORMONE-FREE CULTURE METHOD FOR CITRUS SHOOT TIP

TECHNICAL FIELD

The present invention belongs to the technical field of plant culture, in particular to a hormone-free culture method for a citrus shoot tip.

BACKGROUND

Shoot tip culture is a sterile culture of shoot tip meristem, which can rapidly propagate clones and cultivate virus-free seedlings. At present, shoot tip culture is widely used in rapid propagation of seedlings, variety improvement, virus-free seedling production, and the like. Regenerated plants from shoot tip tissue culture are genetically stable and are especially suitable for species with difficulties in conventional breeding, trees with a long juvenile period, or species that need detoxification.

MS, B5, and White medium are commonly used for shoot tip culture, and other substances such as nutrients and growth regulators are added to improve the seedling rate in shoot tip tissue culture. 2-4% glucose or sucrose is generally used as a carbon source and agar as a curing agent. Plant hormones such as auxin (NAA or IAA), gibberellin (GA3, etc.) and cytokinin (6-BA, zeatin, etc.) are commonly used to promote shoot tip growth and differentiation. The plant hormones for different plant varieties vary greatly in types and concentrations. Shoot tip cultures include two types: common shoot tip culture and shoot tip meristem culture. The survival rate of shoot tip culture is positively correlated with the size of the shoot tip. The common shoot tip culture takes a few millimeters of shoot tip or lateral bud, while the shoot tip meristem culture requires a shoot tip growth point (namely, a growth cone with 1-2 leaf primordial) of less than 0.5 mm. Disease caused by viruses is different from fungal and bacterial diseases, and cannot be controlled by fungicides or antibiotics, or cured in production. Viruses unevenly distribute in plants. Because there is no vascular bundle in the shoot tip growth point, a virus can only be transmitted through plasmodesmata, and cannot keep up with the speed of cell division and growth. Shoot tip culture has a good detoxification effect and stable offspring, which is widely used at present.

The studies on fruit trees and other woody plants are later than those on herbaceous plants because it is difficult to implement woody plant shoot tip culture. There are several reasons for this difficulty, but the most important reason is that the demand for nutrients, especially the demand of shoot tips on hormones is not known clearly. For example, if the concentration of auxin is too low, the shoot tips grow too slowly or not at all, and the cells gradually age, brown, and die. If the concentration of auxin is too high, the callus is generated at the base of the shoot tip after inoculation, and it is easy to produce deformed buds or chimeras, resulting in unstable inheritance of varieties. Therefore, in practice, people have to spend a lot of time determining the appropriate hormone types and concentrations for different varieties.

The culture of citrus shoot tips is generally carried out by MS medium and plant hormones. For different varieties, the types and concentrations of hormones are different, and the operators need to spend a lot of energy on experiments to explore the hormone formula for different varieties.

SUMMARY

An objective of the present invention is to provide a hormone-free culture method for a citrus shoot tip. A high-sugar liquid medium without adding any hormones is provided for culturing the citrus shoot tip. After the citrus shoot tip is cultured, a regenerated citrus seedling is obtained by grafting a micro-bud.

The method of the present invention includes the following steps:

(1) selecting an adult citrus branch, cutting off a leave, washing a dust on a surface of the adult citrus branch, and then cutting into a stem segment with a length of 6-7 cm;

(2) disinfecting the stem segment first with alcohol for 20-30 s and then with a sodium hypochlorite solution for 15-25 min, then washing with sterile water, and finally, removing surface water with a sterile filter paper to obtain a sterilized stem segment;

(3) inserting the sterilized stem segment into a Murashige and Skoog (MS) solid medium, and then placing in an incubator for a branch culture for 10-15 days to allow the stem segment to grow a new bud;

(4) preparing a Murashge and Tucker (MT) liquid medium solution, and separately packaging after sterilization, where a mass concentration of sucrose in the MT liquid medium solution is 7-8%; adding the MT liquid medium solution into a culture dish to prepare a liquid medium, and sealing the liquid medium with a sealing membrane for later use;

(5) removing an outer leave of the new bud, and cutting a shoot tip with a length of 0.15-0.25 mm from a resulting bud by a sterile blade; inoculating the shoot tip in the liquid medium and then placing in an incubator for a primary culture for 25-40 days;

(6) selecting a seed of a trifoliate orange or a citrange and peeling off a testa, disinfecting first with the alcohol for 20-30 s and then with the sodium hypochlorite solution for 15-25 min, and then washing with sterile water to obtain a sterilized rootstock seed;

(7) inoculating the sterilized rootstock seed into a test tube containing the MS solid medium and culturing in dark for 13-15 days to obtain an etiolated seedling with a height of 6-9 cm;

(8) selecting an etiolated seedling with a diameter of a root neck of greater than or equal to 2 mm and placing in a sterile culture dish; cutting off an upper part of a stem of the etiolated seedling and cutting a T-shaped incision at a position of 3-5 mm from an upper end of a resulting stem; placing the shoot tip after the primary culture in a middle of the T-shaped incision to obtain a grafted seedling; and (9) placing the grafted seedling in an incubator for a grafting culture, and then conducting a secondary grafting in a greenhouse when a scion bud grows to 0.5-1 cm.

In the above step (1), the adult citrus branch grows well and has no obvious disease spot on the appearance.

In the above step (2) and step (6), a mass concentration of the alcohol is 70-80%.

In the above step (2) and step (6), a mass concentration of the sodium hypochlorite solution is 1-1.5%.

In the above step (2) and step (6), washing with the sterile water is conducted 3-5 times.

In the above step (1), each stem segment has 3-4 buds.

In the above step (3) and step (9), a culture condition of the incubator is 1600-2200 Lux of a light intensity, and 16 h of light at 25±0.5° C. and 8 h of darkness at 25±0.5° C. per 24 h.

In the above step (5), the outer leave of the new bud is removed and the resulting bud is cut into the shoot tip with the help of a stereoscope in a super-clean worktable.

In the above step (4), separately packaging by 100 ml/bottle after sterilization.

In the above step (4), the culture dish is a glass culture dish with a diameter of 60 mm after sterilization.

In the above step (4), the liquid medium solution is added into several culture dishes on the super-clean worktable.

In the above step (4), an amount of the liquid medium solution added to each culture dish is 3 ml.

In the above step (5), a culture condition of the incubator is 1600-2200 Lux of light intensity, and 16 h of light at 40±0.5° C. and 8 h of darkness at 30±0.5° C. per 24 h.

In the above step (6), a full and healthy seed of the trifoliate orange or the citrange is selected.

In the above step (6), disinfecting and washing are carried out on the super-clean worktable.

In the above step (8), cutting and grafting are carried out on the super-clean worktable.

In the above step (7), a condition of the culturing in the dark is culturing at 25±0.5° C. for 24 h without light.

In the present invention, a high-sugar MT medium is provided to culture the shoot tip of the woody plant citrus. Under a high-sugar concentration, it is not easy for the shoot tip browning. The growth rate is moderate, and no callus is produced. The treatment at 40±0.5° C. is intended to inactivate the virus without affecting the growth of the shoot tip, which ensures the genetic stability of the variety.

According to the present invention, regenerated seedlings are obtained without using hormones, and the efficiency of plant shoot tip culture is significantly improved. The culture method of the present invention has been successfully applied to four citrus varieties: Ehime Kashi No. 28, Navvelina, *Citrus reticulata* 'Chun Jian', and Newhall oranges, indicating that the medium is suitable for a number of citrus varieties and can be widely used in different citrus varieties in the future.

The advantages of the present invention are as follows:
(1) No Limitation on Hormone Concentration.

MS medium and hormone combinations with different concentrations are usually used for the culture of citrus shoot tip. However, due to different varieties of shoot tips have different requirements for hormone types and concentrations, operators have to constantly explore and adjust hormone types and concentrations for the culture of citrus shoot tip, which is time-consuming and laborious, and is not conducive to large-scale popularization. In the present invention, a high-sugar MT medium is provided. Under the high-sugar concentration, it is not easy for the shoot tip browning. The growth rate is moderate, and no callus is produced, which ensures the genetic stability of the variety. The present invention has been successfully applied to four citrus varieties and is expected to be widely used in a number of citrus varieties in the future.

(2) Reduced Difficulty in Micro-Bud Grafting:

The technique of the micro-bud grafting for citrus requires 0.15-0.25 mm of a shoot tip to be grafted to a tiny incision of an etiolated seedling, which requires a high technical requirement of the operator under the stereoscope, and it is hard to see, and the survival rate of the grafting is low. In the present invention, a shoot tip of 0.15-0.25 mm is taken, and grows normally under a high temperature (40±0.5° C.) to inactivate the virus. After 28 days, a shoot tip of 0.25 mm grows to 0.5 mm, and then micro-bud grafting is allowed to be carried out. The operation becomes easy, and the survival rate of the grafting is significantly increased from 50% to at least 90%.

(3) Reduced Production Cost Since the Virus can be Inactivated During Culturing the Shoot Tip:

In previous studies, the detoxification and heat treatment of virus-carrying citrus is carried out by selecting healthy and pure varieties of plants without obvious disease spots, planting in pots, and treating at 40° C. for 16 h, 35° C. for 8 h, and variable temperatures for 1-2 months in a glass greenhouse or a large artificial climate room; peeling off on the shoot tip and grafting micro-bud on a new shoot. The step of the heat treatment in the glass greenhouse or the artificial climate room needs to be carried out in a glass greenhouse or an artificial climate room with an area of more than 10 m$^2$ because of the large number of plants. The construction cost is high, and the operation consumes a lot of electric energy, which results in a high cost. In the method of the present invention, when culturing the citrus shoot tip, the inactivate treatment of the virus under a high temperature is carried out at the same time. The 0.15-0.25 mm of the citrus shoot tip is cut and placed in the 60 mm culture dish, where only 3 ml of the liquid medium is needed, and the heat treatment is carried out in an ordinary incubator. An incubator with a capacity of 200 L can help treat hundreds of different samples at the same time. This method for culturing does not require production units to build the glass greenhouse or the artificial climate room for heat treatment, saves a lot of electric energy consumption, and uses a small amount of medium. The present invention saves a lot of hardware construction and operation costs and is more in line with the current environmental protection requirements of energy saving and emission reduction.

(4) Wide Application Prospects:

At present, the culture of citrus shoot tip is generally carried out by MS medium and plant hormones. For different varieties, the types and concentrations of hormones are different, and the operators need to spend a lot of energy on experiments to explore the hormone formula for different varieties. The present invention adopts a high-sugar MT medium to carry out the shoot tip culture and the micro-bud grafting on four citrus varieties: Ehime Kashi No. 28, Navvelina, *Citrus reticulata* 'Chun Jian', and Newhall oranges, respectively. Without using hormones, regenerated citrus seedlings can be obtained efficiently, and the efficiency of citrus shoot tip culture can be significantly improved. The virus is inactivated by the heat treatment in a form of day and night alternating in the shoot tip culture, which could avoid the production unit to build a glass greenhouse or a large artificial climate room for the heat treatment and a large amount of electric energy consumption in. This method can significantly save cost and energy and increase efficiency, which is conducive to the large-scale production of citrus seedlings.

DETAILED DESCRIPTION OF THE EMBODIMENTS

Citrus varieties such as Ehime Kashi No. 28, Navvelina, *Citrus reticulata* 'Chun Jian', and Newhall oranges are adopted in the embodiments of the present invention.

The survival rate of culturing is at least 95% in the embodiments of the present invention.

The adult citrus branch grows well and has no obvious disease spot on the appearance in the embodiments of the present invention.

A full and healthy seed of the trifoliate orange or the citrange is selected in the embodiments of the present invention.

The condition of the culturing in the dark is culturing at 25±0.5° C. for 24 h without light in the embodiments of the present invention.

Embodiment 1

(1) An adult citrus branch is selected, leaves are cut off, the dust on the surface of the adult citrus branch are washed, and then the adult citrus branch is cut into 7 cm long stem segments. Each stem segment has 4 buds.

(2) First the stem segment is disinfected with alcohol for 30 s, then disinfected with the sodium hypochlorite solution for 25 min, then washed with sterile water, and finally, surface water of the stem segment is removed with the sterile filter paper to obtain a sterilized stem segment. The mass concentration of the alcohol is 70%, the mass concentration of the sodium hypochlorite solution is 1%, and the stem segment is washed with sterile water 5 times.

(3) The sterilized stem segment is inserted into the MS solid medium, and then placed in an incubator for the branch culture for 15 days to allow the stem segment to grow a new bud. The culture condition of the incubator is 1600 Lux of the light intensity, and 16 h of light at 25±0.5° C. and 8 h of darkness at 25±0.5° C. per 24 h.

Figure 1:
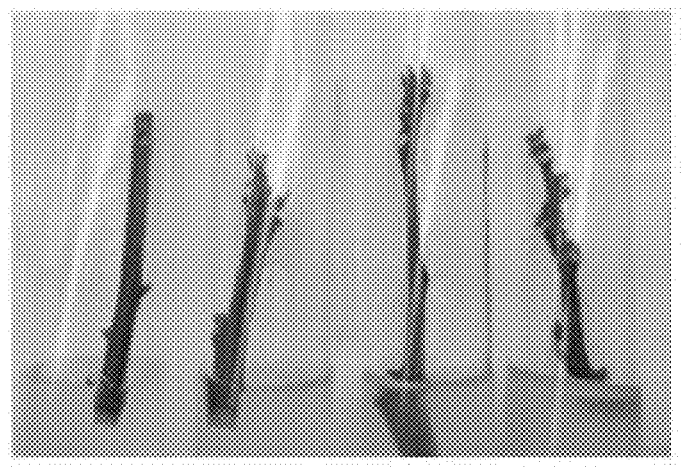
FIG. 1 is a photo showing an appearance of branches growing new buds in embodiment 1 of the present invention.

The appearance of the stem segment with new buds is shown in FIG. 1.

(4) The MT liquid medium solution is prepared and separately packaged after sterilization where the mass concentration of sucrose is 8%. The liquid medium solution is added into a culture dish to prepare a liquid medium, and the liquid medium is sealed with a sealing membrane for later use. The MT liquid medium solution is separately packaged by 100 ml/bottle after sterilization. The culture dish is a glass culture dish with a diameter of 60 mm after sterilization. The liquid medium solution is added into several culture dishes on the super-clean worktable. An amount of the liquid medium solution added to each culture dish is 3 ml.

(5) The new bud is taken and the outer leave of the bud is removed, and a shoot tip with a length of 0.25 mm is cut by a sterile blade. The shoot tip is inoculated in the liquid medium and then placed in an incubator for a primary culture for 40 days. The outer leave of the new bud is removed and the resulting bud is cut into the shoot tip with the help of a stereoscope in a super-clean worktable. The culture condition of the incubator is 1600 Lux of the light intensity, and 16 h of light at 40±0.5° C. and 8 h of darkness at 30±0.5° C. per 24 h.

Figure 2:
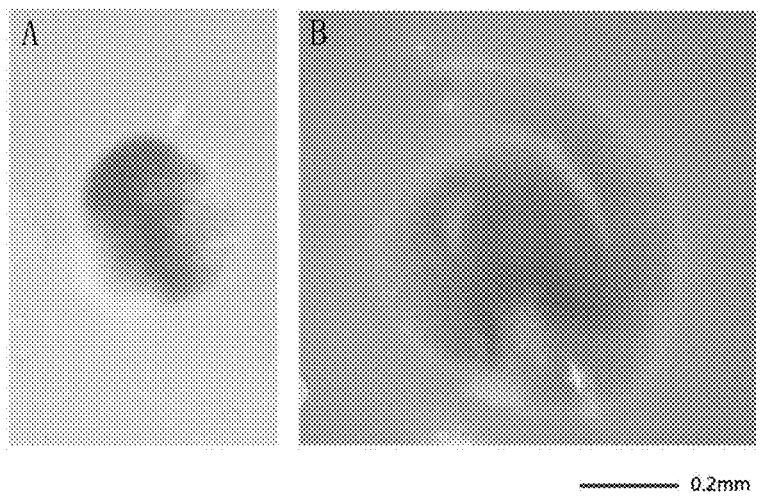
FIG. 2 is a photo showing an appearance of a shoot tip after a primary culture in embodiment 1 of the present invention, where A is cultured for 3 days, and B is cultured for 4 weeks.

The shoot tip cultured 3 days and 4 weeks of the primary culture is shown in FIGS. 2A and 2B, respectively.

(6) A seed of a trifoliate orange is selected and peeled off a testa, first the resulting seed is disinfected with the alcohol for 30 s, then disinfected with the sodium hypochlorite solution for 25 min, and then washed with sterile water to obtain a sterilized rootstock seed. The mass concentration of the alcohol is 70%. The mass concentration of the sodium hypochlorite solution is 1%. Washed with sterile water 5 times. Disinfecting and washing are carried out on the super-clean worktable.

(7) The sterilized rootstock seed is inoculated into a test tube containing the MS solid medium and cultured in the dark for 14 days to obtain an etiolated seedling with a height of 7-8 cm.

Figure 3:
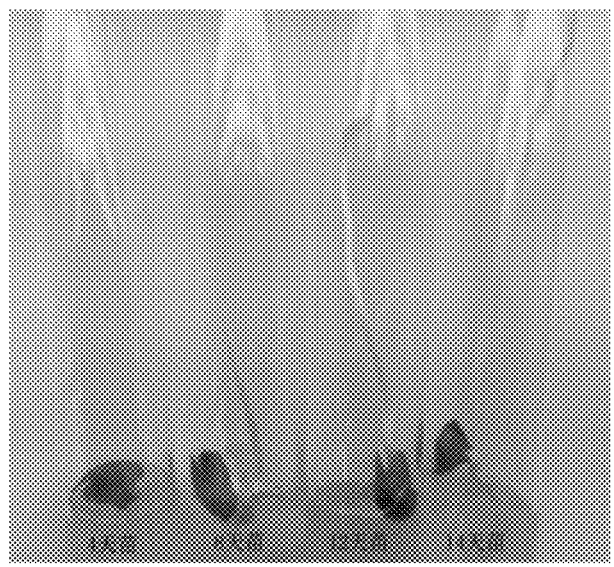
FIG. 3 is a photo showing an appearance of etiolated seedlings in embodiment 1 of the present invention.

The appearance of the etiolated seedling cultured in the dark for 4, 8, 12, and 14 days is shown in FIG. 3.

(8) The etiolated seedling with a diameter of a root neck of greater than or equal to 2 mm is selected and placed on a sterile culture dish. An upper part of the stem of the etiolated seedling is cut off and a T-shaped incision at the position of 3-5 mm from the upper end of the resulting stem is cut. The shoot tip after the primary culture is placed in the middle of the T-shaped incision to obtain a grafted seedling. Cutting is carried out on the super-clean worktable.

(9) The grafted seedling is placed in an incubator for a grafting culture on the super-clean worktable, and then a secondary grafting is conducted in the greenhouse when the scion bud grows to 0.8 cm. The culture condition of the incubator is 1600 Lux of the light intensity, and 16 h of light at 25±0.5° C. and 8 h of darkness at 25±0.5° C. per 24 h.

Figure 4:
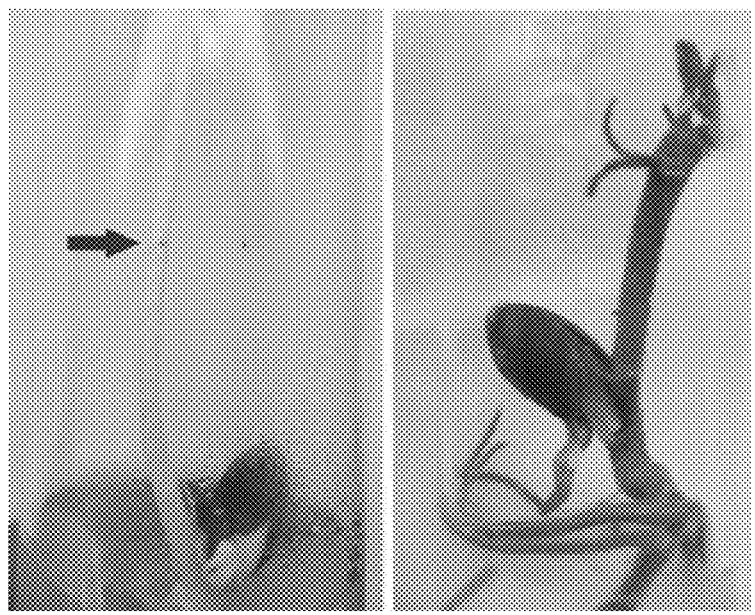
FIG. 4 is a photo showing an appearance of a micro-bud grafting and scion buds growing to 0.5 cm after the grafting in embodiment 1 of the present invention. In the figure, the left figure is a grafted seedling that completed the micro-bud grafting, and the right figure is the grafted seedlings with the scion buds growing to 0.5 cm.

The appearance of the micro-bud grafting and scion buds growing to 0.5 cm after the grafting is shown in FIG. 4.

Embodiment 2

This embodiment differs from Embodiment 1 in the following:

(1) 6 cm long stem segments are cut and each stem segment has 3 buds.

(2) Disinfect with alcohol for 25 s, then disinfect with sodium hypochlorite solution for 20 min. The mass concentration of the alcohol is 75%. The mass concentration of the sodium hypochlorite solution is 1.3%. Washed with sterile water 4 times.

(3) The stem segment is cultured for 13 days, and the light intensity of the incubator is 2000 Lux.

(4) The mass concentration of sucrose is 8% in the MT liquid medium solution.

(5) The new bud is taken and the outer leave of the bud is removed, and a shoot tip with a length of 0.2 mm is cut by a sterile blade. The primary culture lasts for 30 days. The light intensity of the incubator is 2000 Lux.

(6) A seed of the citrange is selected, disinfected with alcohol for 25 s, then disinfected with the sodium hypochlorite solution for 20 min. The mass concentration of the alcohol is 75%. The mass concentration of the sodium hypochlorite solution is 1.3%. Washed with sterile water 4 times.

(7) Cultured in the dark for 13 days to obtain an etiolated seedling with a height of 6-7 cm.

(8) A T-shaped incision at the position of 3 mm from the upper end of the stem is cut.

(9) A secondary grafting is conducted when the scion bud grows to 0.5 cm. The light intensity of the incubator is 2000 Lux.

Embodiment 3

This embodiment differs from Embodiment 1 in the following:

(1) 6.5 cm long stem segments are cut, and each stem segment has 3 buds.

(2) Disinfect with alcohol for 20 s, then disinfect with sodium hypochlorite solution for 15 min. The mass concentration of the alcohol is 80%. The mass concentration of the sodium hypochlorite solution is 1.5%. Washed with sterile water 3 times.

(3) The stem segment is cultured for 10 days, and the light intensity of the incubator is 2200 Lux.

(4) The mass concentration of sucrose is 7% in the MT liquid medium solution.

(5) The new bud is taken and the outer leave of the bud is removed, and a growing point of the shoot tip with a length of 0.15 mm is cut by a sterile blade. The primary culture lasts for 25 days. The light intensity of the incubator is 2200 Lux.

(6) A seed of the citrange is selected, disinfected with alcohol for 20 s, then disinfected with the sodium hypochlorite solution for 15 min. The mass concentration of the alcohol is 80%. The mass concentration of the sodium hypochlorite solution is 1.5%. Washed with sterile water 3 times.

(7) Cultured in the dark for 15 days to obtain an etiolated seedling with a height of 8-9 cm.

(8) A T-shaped incision at the position of 5 mm from the upper end of the stem is cut.

(9) A secondary grafting is conducted when the scion bud grows to 1 cm. The light intensity of the incubator is 2200 Lux.

What is claimed is:

1. A hormone-free culture method for a citrus shoot tip, comprising the following steps:
   (1) selecting an adult citrus branch, cutting off a leave, washing a dust on a surface of the adult citrus branch, and then cutting into a stem segment with a length of 6-7 cm;
   (2) disinfecting the stem segment first with alcohol for 20-30 s and then with a sodium hypochlorite solution for 15-25 min, then washing with sterile water, and finally, removing surface water with a sterile filter paper to obtain a sterilized stem segment;
   (3) inserting the sterilized stem segment into a Murashige and Skoog (MS) solid medium, and then placing in an incubator for a branch culture for 10-15 days to allow the sterilized stem segment to grow a new bud;
   (4) preparing a Murashge and Tucker (MT) liquid medium solution, and separately packaging after sterilization, wherein a mass concentration of sucrose in the MT liquid medium solution is 7-8%; adding the MT liquid medium solution into a culture dish to prepare a liquid medium, and sealing the liquid medium with a sealing membrane for later use;
   (5) removing an outer leave of the new bud, and cutting a shoot tip with a length of 0.15-0.25 mm from a resulting bud by a sterile blade; inoculating the shoot tip in the liquid medium and then placing in an incubator for a primary culture for 25-40 days;
   (6) selecting a seed of a trifoliate orange or a citrange and peeling off a testa, disinfecting first with the alcohol for 20-30 s and then with the sodium hypochlorite solution for 15-25 min, and then washing with the sterile water to obtain a sterilized rootstock seed;
   (7) inoculating the sterilized rootstock seed into a test tube containing the MS solid medium and culturing in dark for 13-15 days to obtain an etiolated seedling with a height of 6-9 cm;
   (8) selecting an etiolated seedling with a diameter of a root neck of greater than or equal to 2 mm and placing in a sterile culture dish; cutting off an upper part of a stem of the etiolated seedling and cutting a T-shaped incision at a position 3-5 mm from an upper end of a resulting stem; placing the shoot tip after the primary culture in a middle of the T-shaped incision to obtain a grafted seedling; and
   (9) placing the grafted seedling in an incubator for a grafting culture, and then conducting a secondary grafting in a greenhouse when a scion bud grows to 0.5-1 cm.

2. The hormone-free culture method for the citrus shoot tip according to claim 1, wherein in step (2) and step (6), a mass concentration of the alcohol is 70-80%.

3. The hormone-free culture method for the citrus shoot tip according to claim 1, wherein in step (2) and step (6), a mass concentration of the sodium hypochlorite solution is 1-1.5%.

4. The hormone-free culture method for the citrus shoot tip according to claim 1, wherein in step (2) and step (6), washing with the sterile water is conducted 3-5 times.

5. The hormone-free culture method for the citrus shoot tip according to claim 1, wherein in step (1), each stem segment has 3-4 buds.

6. The hormone-free culture method for the citrus shoot tip according to claim 1, wherein in step (3) and step (9), a culture condition of the incubator is 1600-2200 Lux of a light intensity, and 16 h of light at 25±0.5° C. and 8 h of darkness at 25±0.5° C. per 24 h.

7. The hormone-free culture method for the citrus shoot tip according to claim 1, wherein in step (5), the outer leave of the new bud is removed and the resulting bud is cut into the shoot tip with the help of a stereoscope in a super-clean worktable.

8. The hormone-free culture method for the citrus shoot tip according to claim 1, wherein in step (5), a culture condition of the incubator is 1600-2200 Lux of light intensity, and 16 h of light at 40±0.5° C. and 8 h of darkness at 30±0.5° C. per 24 h.

* * * * *